(12) United States Patent
Kollefrath et al.

(10) Patent No.: US 7,789,663 B2
(45) Date of Patent: Sep. 7, 2010

(54) PROCESS FOR THE RETRACTION OF SULCUS

(75) Inventors: Ralf Kollefrath, Ruethi (CH); Stephan Lampl, Luchingen (CH); Dierk Lubbers, Altstatten (CH)

(73) Assignee: Coltene AG, Altstatten (CH)

( * ) Notice: Subject to any disclaimer, the term of this patent is extended or adjusted under 35 U.S.C. 154(b) by 0 days.

(21) Appl. No.: 11/075,031

(22) Filed: Mar. 8, 2005

(65) Prior Publication Data
US 2005/0202367 A1    Sep. 15, 2005

Related U.S. Application Data

(63) Continuation-in-part of application No. 10/686,195, filed on Mar. 15, 2004, now abandoned.

(30) Foreign Application Priority Data
Feb. 22, 2005    (EP)    ................... 05101327

(51) Int. Cl.
A61C 5/14    (2006.01)
A61C 19/00    (2006.01)
(52) U.S. Cl. ..................... 433/136
(58) Field of Classification Search ............... 433/136, 433/214, 138, 37, 38, 215
See application file for complete search history.

(56) References Cited

U.S. PATENT DOCUMENTS 3,304,608 A    2/1967    Frohnecke
(Continued)

FOREIGN PATENT DOCUMENTS

DE    3737552    5/1989
(Continued)

OTHER PUBLICATIONS

United States Office Action dated Apr. 10, 2007 and list of references cited from corresponding U.S. Appl. No. 11/361,100.
(Continued)

*Primary Examiner*—Cris L Rodriguez
*Assistant Examiner*—Heidi M Eide
(74) *Attorney, Agent, or Firm*—Katten Muchin Rosenman LLP

(57) ABSTRACT

The invention relates to a process of retraction of sulcus, comprising the steps of: applying a silicone material onto and/or at the vicinity of the boundary of a tooth and adjacent sulcus, which silicone material expands during or after its curing reaction; applying a cap onto said tooth, thereby forming a chamber over said silicone material, wherein said chamber comprises as its walls the tooth, the cap and an outer section of said sulcus; whereby said chamber allows for the silicone material to expand into the crevice between sulcus and tooth. Said cap is at least partially filled with a plastically deformable material when applied onto said tooth in step; and/or said cap is deformable, especially under biting pressure.

2 Claims, 2 Drawing Sheets

U.S. PATENT DOCUMENTS

| | | | |
|---|---|---|---|
| 3,357,104 A | 12/1967 | Greene et al. | |
| 3,390,458 A | 7/1968 | Lytton | |
| 3,602,993 A | 9/1971 | Kenney | |
| 3,686,754 A | 8/1972 | Kondoloff | |
| 3,742,605 A | 7/1973 | Cooper | |
| 4,255,140 A | 3/1981 | Marshall | |
| 4,483,675 A | 11/1984 | Marshall | |
| 4,531,914 A | 7/1985 | Spinello | |
| 4,677,139 A * | 6/1987 | Feinmann et al. | 128/888 |
| 4,805,201 A * | 2/1989 | Strong-Grainger | 378/169 |
| 5,385,469 A * | 1/1995 | Weissman | 433/40 |
| 5,676,543 A | 10/1997 | Dragan | |
| 6,398,761 B1 | 6/2002 | Bills et al. | |
| 6,769,913 B2 | 8/2004 | Hurson | |
| 6,890,177 B2 | 5/2005 | Dragan | |
| 7,033,173 B2 | 4/2006 | Coopersmith | |
| 7,153,134 B2 | 12/2006 | Coopersmith | |
| 7,189,075 B2 | 3/2007 | Dragan | |
| 7,195,483 B2 | 3/2007 | Dragan | |
| 7,241,143 B2 | 7/2007 | Discko, Jr. et al. | |
| 2003/0190584 A1* | 10/2003 | Heasley | 433/136 |
| 2004/0106086 A1 | 6/2004 | Dragan | |
| 2004/0126740 A1 | 7/2004 | Coopersmith | |
| 2004/0265777 A1* | 12/2004 | Heasley | 433/136 |
| 2005/0069838 A1 | 3/2005 | Kollefrath et al. | |
| 2005/0118552 A1 | 6/2005 | Coopersmith | |
| 2005/0202367 A1 | 9/2005 | Kollefrath et al. | |
| 2007/0065770 A1 | 3/2007 | Lubbers et al. | |
| 2007/0087304 A1 | 4/2007 | Discko, Jr. et al. | |
| 2007/0128581 A1 | 6/2007 | Dustan-Maher | |
| 2007/0160952 A1 | 7/2007 | Kollefrath et al. | |
| 2007/0259313 A1 | 11/2007 | Dragan et al. | |
| 2009/0061393 A1 | 3/2009 | Kollefrath et al. | |

FOREIGN PATENT DOCUMENTS

| | | |
|---|---|---|
| DE | 9211339 | 11/1992 |
| EP | 0 092 329 | 10/1983 |
| WO | 2004000153 | 12/2003 |
| WO | 2005051219 | 6/2005 |

OTHER PUBLICATIONS

United States Office Action dated Nov. 16, 2007 and list of references cited from corresponding U.S. Appl. No. 11/361,100.
United States Office Action dated May 20, 2008 from corresponding U.S. Appl. No. 11/361,100.
United States Office Action dated Sep. 5, 2008 from corresponding U.S. Appl. No. 11/361,100.
United States Office Action dated Oct. 2, 2008 from corresponding U.S. Appl. No. 11/361,100.
United States Office Action dated Jun. 1, 2009 from corresponding U.S. Appl. No. 11/361,100.
"Vivo" made by Corpura, B.V. dated Feb. 26, 2003 pp. 3-5.
United States Office Action dated May 3, 2006 from corresponding U.S. Appl. No. 10/686,195.
United States Office Action dated Oct. 23, 2006 from corresponding U.S. Appl. No. 10/686,195.
International Search Report dated Mar. 17, 2004 from PCT/CH03/00798.
United States Office Action dated Oct. 24, 2008 from corresponding U.S. Appl. No. 11/546,754.
Office Action dated Feb. 5, 2009 from corresponding U.S. Appl. No. 11/546,754.
Office Action dated Jan. 16, 2008 from corresponding U.S. Appl. No. 11/724,093.
Office Action dated Oct. 20, 2008 from corresponding U.S. Appl. No. 11/724,093.
Notice of References Cited from corresponding U.S. Appl. No. 11/724,093 (issued with the Supplemental Notice of Allowability dated May 14, 2009).
Dr. M. Martignoni "Precision and Contour in Prosthetic Reconstruction" Quintessenz Verlags-GmbH, 1987. Translation of pp. 117-126 attached.

* cited by examiner

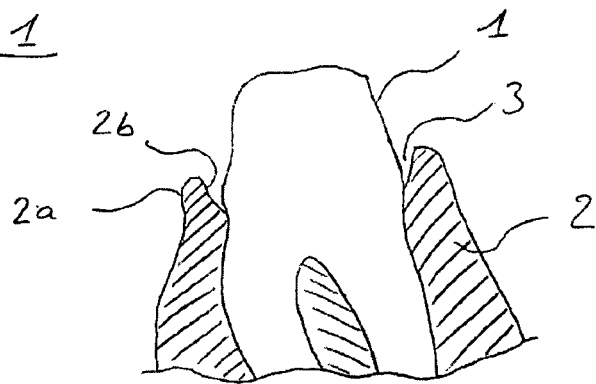
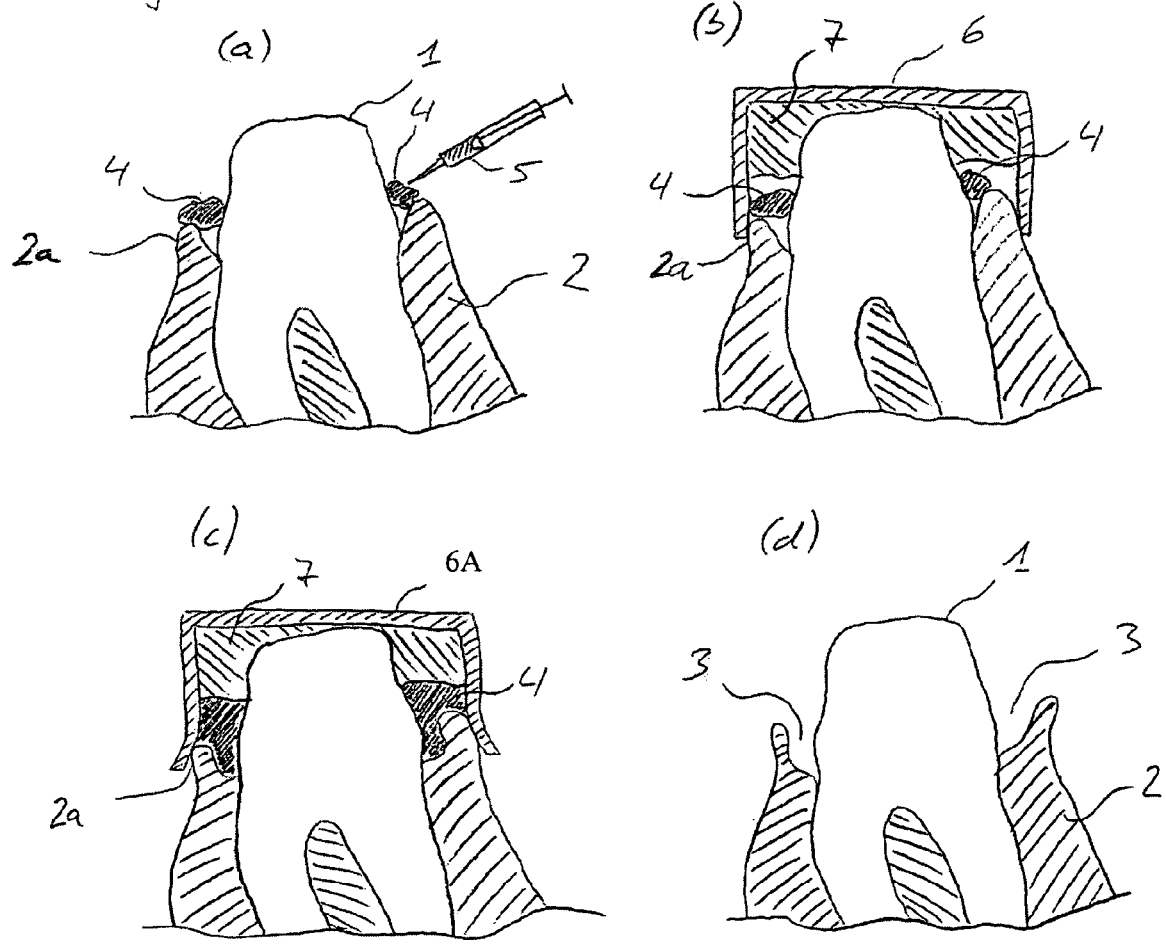

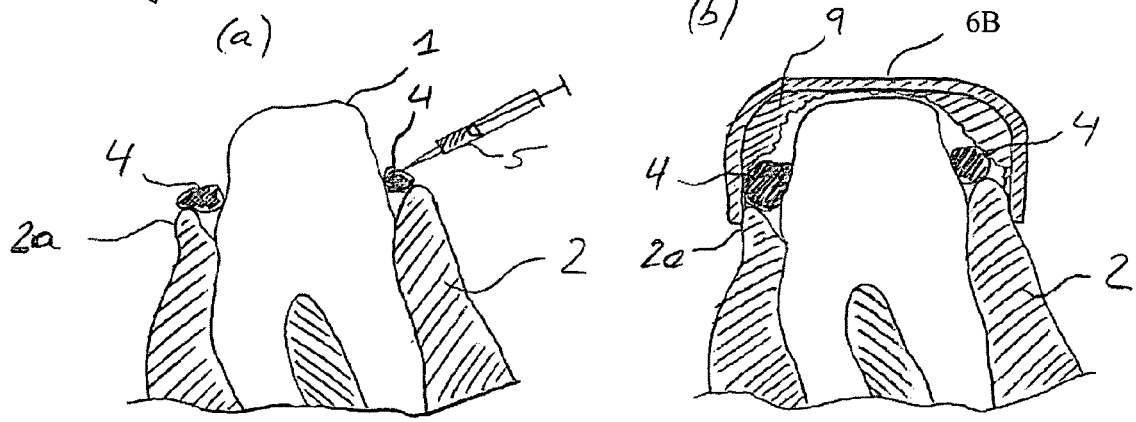
Fig. 3
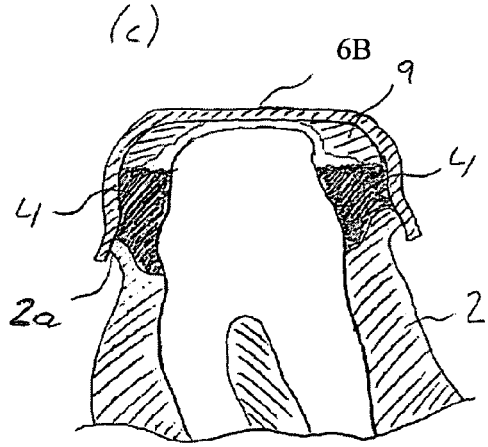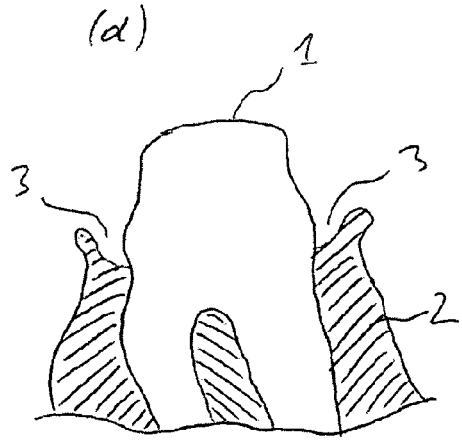
Fig. 4
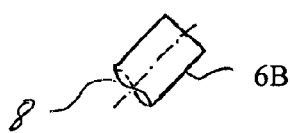

PROCESS FOR THE RETRACTION OF SULCUS

CROSS REFERENCE TO RELATED APPLICATION

This application is a continuation-in-part of U.S. application Ser. No. 10/686,195 filed on Mar. 15, 2004, now abandoned and claims priority from European Patent Application EP05101327.4 filed on Feb. 22, 2005, the contents of which are herein wholly incorporated by reference.

The present invention relates to the field of dental restoration, more precisely to a process for the retraction of sulcus according to the independent claims.

For a preparation of a dental prosthesis, an impression of the teeth and the part of the jaw adjacent to these teeth must be provided to the dental technician. Especially, a correct impression of the sub-gingival area of the tooth is important in dental restoration. Therefore, an impression of the dental situation has to be prepared by the dentist. In order to cover the transitional area of tooth and jaw, it is necessary to free the neck of the tooth which is covered by the gingiva. Thus, for preparing the dental impression, the sulcus must widened, i.e. the sulcus and/or the gingival must be retracted and the neck of the tooth be exposed.

Beside a widely used method which relies on the insertion of a retraction cord into the sulcus, U.S. Pat. No. 5,676,543 describes an alternative method: A mold of the dental situation is prepared by a curable molding mass. The cured impression is subsequently removed. A layer of a syringable and curable material is applied into the mold and the thus prepared mold is placed onto the teeth again. Mandatory, the syringable and curable material needs to contain an astringent or a substance causing tissue retraction. By exerting pressure onto the mold, the curable material is pressed in the area between the neck of the tooth and the gingiva. Due to the hemostatic compound and the hydrostatic pressure of the silicone, a tissue contraction is caused, and the sulcus retracts from the neck of the tooth. A proper impression of the dental situation including the uncovered sulcus can be made after cleaning. However, a major drawback in practice is that the application of the syringable, curable material into the negative dental impression not always leads to the required results. During the reinsertion of the mold, the syringable material is often substantially smeared so that a correct sulcus retraction is no longer guaranteed. Moreover, the contraction of the sulcus by the astringent is not always sufficient in order to guarantee the quality of the mold. Furthermore, the proper quantity of syringable material to be applied proves to be difficult to find since during application the contours of the negative mold are covered and thus no control of the layer thickness is longer possible. Besides the mentioned drawbacks, the necessity of providing an astringent unwantedly complicates the overall composition of the syringable material.

Another method of cordless retraction of gingival sulcus is disclosed in US 2004/0106086. Therein, in contrast to U.S. Pat. No. 5,676,543, a dental impression material is used for widening the gingival crevice adjacent to the tooth. The dental impression material may either be provided into a dental dam, and then the dental dam is placed over the teeth and adjacent gingival, or the impression material is firstly placed onto the tooth and gingival, and the dental dam is then placed on top of it. According to that invention, the dental dam is made of a porous foam or sponge type material, thereby facilitating subsequent removal of the dam together with the set impression material. A drawback of this technique is the dental dam, which is seated on adjacent teeth and therefore is not suitable for complicated dental situations. Moreover, a substantial content of an astringent is again, as in U.S. Pat. No. 5,676,543, to be contained in the impression material in order to assure retraction of the gingival.

US patent application 2004/0265777 discloses a different approach of gingival retraction by suggesting retraction devices which may be inserted into the gingival sulcus in a single motion by direct transmission of vertical forces circumferentially through the rigidity of a structural backing component to laterally displace the gingival tissue around a tooth. This approach, however, is hampered by the fact that the gingival tissue is likely to be harmed by inserting the device directly into the crevice of tooth and gingival.

Yet another method of sulcus retraction is disclosed in EP 1 459 701 A1, wherein firstly an impression mold is taken and the impression mold subsequently removed, secondly a silicone material is applied onto the boundary of sulcus and tooth, which silicone material expands upon curing. Upon reinsertion of the impression mold after appliance of the silicone material, the silicone material expands into the gingival crevice and widens it. However, this two-step approach of impression molding and retraction of sulcus is relatively time-consuming. Alternatively, the use of hollow cotton rolls is suggested in WO 2004/082510; however, sufficient direction of the expanding silicone material into the sulcus can not be achieved with any dental situation by using such cotton rolls.

A further approach for the retraction of gingival margins is disclosed in EP 92 329, using foam silicone material. According to EP 92 329, the complete tooth and surrounding gingival tissue is covered by the silicone material, and may be held in place by a carrier such as a spoon. As the expansion of the silicone material is thereby only insufficiently directed into the sulcus, no satisfactory sulcus retraction is however achieved in practice.

The object of the invention is to avoid the disadvantages of the prior art, especially to provide an alternative method and cap for uncovering the neck of a tooth by retraction of sulcus, which is more convenient for the patient, less time-consuming and more reliable. This problem is solved by a method, a cap and a dental kit according to the features of the independent claims.

The claimed process of retraction of sulcus comprises the steps of:

i. applying an elastomeric material, preferably a silicone material, a polyurethane material and/or a polyether material onto and/or at the vicinity of sulcus, which elastomeric material expands and cures, particularly expands during or after its curing reaction;

ii. applying a cap onto said tooth, thereby forming a chamber over said silicone material, wherein said chamber comprises as its walls the tooth, the retraction cap and an outer section of said gingiva;

whereby said chamber allows for the elastomeric material to expand into the crevice between sulcus and tooth, characterized in that said cap is at least partially filled with a plastically deformable material when applied onto said tooth in step ii.;

and/or that said cap is deformable, especially under biting pressure.

Additionally or alternatively, a process of retraction of sulcus according to the invention comprises the steps of:

i. At least partially filling an elastomeric material, preferably a silicone material, a polyurethane material and/or a polyether material, into a cap, which elastomeric material expands during or after its curing reaction;

ii. applying said cap onto a tooth, thereby forming a chamber over said elastomeric material (4), wherein said chamber comprises as its walls the tooth, the cap and an outer section of said gingiva;

whereby said chamber allows for the elastomeric material (4) to expand into the sulcus (3), and wherein said cap (6) is deformable, especially under biting pressure. Of course, a plastically deformable, preferably malleable material may be provided additionally into the cap, besides the elastomeric material that expands and cures, prior to application of the cap onto the tooth.

Although some expandable polyurethane-based and/or polyether-based elastomeric materials were recently reported to be physiologically acceptable, silicone materials are currently preferably used as elastomeric material, that expands and cures in the context of the present invention. Mixtures of polyurethane-based, polyether-based and silicone-based materials may be employed as well; suitable mixtures of these materials can be identified by routine experiments of those skilled in the art. Preferably, the elastomeric material is to be removed after curing together with the cap by only one hand grip, preferably also together with the plastically deformable material, due to physical and/or chemical adherence to the suitably chosen cap material, e.g. a compatible silicone material or an open-cell foam material.

In contrast to e.g. US 2004/0106086, the cap is not to be forced into the crevice of the sulcus, but rather is applied suchlike onto the tooth to form a chamber, which chamber comprises as its walls the tooth, the retraction cap and an outer section of said gingiva, i.e. the cap is seated on said outer section of the gingival, thereby said chamber comprising the whole sulcus. Thus, a cap needs not and preferably does not have the internal stability and thin outer wall dimensions which are necessary to mechanically retract the sulcus from a tooth. Rather, the cap is preferably deformable suchlike to allow for a smooth fit to an outer section of the gingiva e.g. under biting pressure, without affecting the integrity of the sulcus.

In any case, the necessary amount of the expandable elastomeric material (possessing a characteristic volume expansion upon curing) and the enclosed free volume of said chamber have to be chosen suchlike and co-ordinated to allow for a direction of the expansion of said expandable elastomeric material into the sulcus by limiting the free space in the cap. Preferably, the cap provides means in its interior to limit the upper expansion of said elastomeric material, and instead directs it into the sulcus. Such limiting means may e.g. be a loose or tight filling material in said interior of the cap, or a plastically deformable material.

As an expandable silicone material suitably applied onto and/or at the vicinity of the boundary of a tooth and adjacent sulcus in step i., the same expandable silicone materials may be used as disclosed in EP 1,459,701; with respect to these silicone materials, the disclosure of EP 1,459,701 is incorporated herein by reference. The silicone material which expands during curing can consist of only one silicone compound or a mixture of different silicone compounds. Preferably this expanding silicone material comprises a minimal expansion of at least 20% upon or after curing, more preferred of at least 30% and most preferred of at least 70% relative to the original volume. The values of this volume expansion is related to the expansion of the material in a non-limited, i.e. in an open volume. The term expanding as used herein is to be understood in that the volume expansion occurs during or after the curing reaction of the silicone material or the mixture of several silicone compounds. Curing reactions are to be understood as reaction processes which lead to the generation of new inter- or intramolecular bonds. The expansion usually will start delayed after the beginning of these reaction processes and will last beyond the end of these reactions. Suitable silicone compounds which exhibit such an expansion behaviour are silicone compounds crosslinkable by addition reactions. An expanding silicone material exhibiting the above mentioned expansion volume allows an improved and simpler control of the sulcus retraction. If found appropriate, a curing catalyst may be added prior to the application of the silicone material, or the silicone material already includes a catalyst which initiates the curing due to ambient humidity. In addition to the specific expansion behaviour of expandable material itself, a further control can also be achieved due to the amount applied. Both factors thus influence mutually the result of the retraction. As currently most advantageous is considered an expandable, addition crosslinkable silicone material which is used as a two component system. The different functionalized poly(dimethyl)siloxanes, for example hydrogen-, dihydroxy- or divinyl-poly(dimethyl)siloxanes used as essential constituents of these two components exhibit a viscosity of preferably between 5 and 100 Pa·s. Expansion occurs due to the release of a gaseous compound, e.g. hydrogen, during the crosslinking-reaction. Both components may further comprise additional fillers which commonly are used for dental masses. These fillers may either be surface treated or be without any surface treatment. Examples of suitable fillers are silica, pyrogeneous silica, calcium carbonate, milled quartz or silicates, albeit the invention is not limited to the presence of these or other fillers. The use of silicone materials crosslinkable by addition reactions furthermore avoids adverse effects to the health of the patient since during curing no harmful compounds are released, i.e. are cleaved. After the curing of the expanding silicone material, it can be routinely removed together with the plastically deformable material previously applied onto said tooth in step ii. The inner diameter of the cap is chosen suchlike to allow for an intimate contact to towards an outer section of said sulcus, i.e. preferably an inner diameter is chosen which slightly exceeds the diameter of the preferably already prepared tooth.

In contrast to EP 1 459 701, said cap is at least partially filled with a plastically deformable material when applied onto said tooth in step ii.; and/or said cap is deformable, especially under biting pressure to allow for a smooth fit to the gingival, especially an outer section of the sulcus. Both these means allow for a more efficient and reliable formation of a chamber over said silicone material than is known in the prior art, wherein said chamber comprises as its walls the tooth, the retraction cap and an outer section of said sulcus. Whereas in EP 1 459 701 a relatively time-consuming two-step process of impression molding and subsequent sulcus retraction is disclosed, according to the present invention a one-step process of impression molding and sulcus retraction is disclosed, which is less time-consuming. The still plastically deformable material is uncured and/or not yet hardened when applied onto the tooth in step ii., thereby allowing for simultaneous impression molding and sulcus retraction. Moreover, due to the application of the plastically deformable material into the cap and subsequent placing of the cap onto the tooth, a more reliable contact of said plastically deformable material to the expandable silicone material can be achieved due to the flowability of the plastically deformable material. The formation of a chamber for the expanding silicone material is thus more reliable and easily achievable as in the prior art. As a plastically deformable material to be placed into the cap, especially silicone materials such as those disclosed in EP 1 459 701 as dental impression materials; with respect to such silicone based dental impression materials, EP 1 459 701 is incorporated herein by reference. Usually these systems consist of at least one silicone compound and a catalyst for the curing. Preferably, silicone compounds being crosslinkable by condensation and, preferably, addition reactions are used. Both components for the mold can either be provided separately and mixed not until the application, or they form a mixture which by humidity or the like is subjected to a curing step.

In contrast to EP 92 329, the expansion to the silicone material is more efficiently directed into the sulcus due to the reliable formation of a chamber over said silicone material, either due to the cap being at least partially filled with a plastically deformable material when applied onto said tooth in step ii.; and/or said cap being deformable.

Especially where the dental situation allows for it, a cap is also understood herein as to comprise a dam-like design such as common impression trays or a cylinder comprising an especially two- or three sides open trough, as long as an efficient formation of a chamber for the expanding silicone material is not hampered, thereby directing the expansion of said silicone material into the gingival crevice. Three sides open troughs in dental dams are e.g. known from US 2004/0106086, incorporated herein by reference with respect to its disclosure of dental dams. Of course, also caps may be used that do not completely cover the tooth, but which are rather secured around the tooth, such as two-sides open tubes, which on one side tightly fitted to the circumference of the tooth, and on the other side are placed onto the gingiva. However, a cap design as a virtually cylindrical, hollow, at one side closed body is preferred. The caps may be provided and supplied in series, connected to each other and easily detachable from each other by a clinician e.g. by means of a scissors. Besides facilitating storage of the caps, this moreover allows for easy appliance of caps to adjacent teeth, if necessary.

According to an especially preferred embodiment, a cap is used in the process according to the invention, the borderline of which cap at its open end virtually resembles the natural wavelike boundary of sulcus surrounding a tooth. Especially with anterior teeth, the wavelike boundary of sulcus and tooth is pronounced, whereas with molar teeth said boundary is less pronounced. In any case, a cap closely resembling said boundary is especially suitable for efficiently forming a chamber for the silicone material to expand into the crevice between sulcus and tooth. The wave-like boundary at the open end of the cap may either be provided pre-made to the clinician, preferably in a variety of different wave-geometries in order to fit for either anterior or molar teeth, or may be individually adapted by the clinician to the specific boundary geometry of the patient's sulcus.

Preferably, the tooth is prepared for receiving a dental restoration, such as e.g. a crown, prior to applying the expandable silicone material onto and/or at the vicinity of the boundary of sulcus and tooth.

If found appropriate, at least one hemostatic compound may be applied to the area adjacent and onto the boundary of tooth and gingiva prior to the application of the silicone material. It may be necessary to rinse off the hemostatic compound before applying the expandable silicone material. Otherwise, remaining hemostatic compound may occasionally hamper the curing reaction of said silicone material. Alternatively or additionally, the expandable silicone material may comprise at least one hemostatic compound. Suitable hemostatic compounds are routinely known and applied by the person of routine skill in the art and are preferably selected from the group consisting of potassium aluminum sulfate, aluminum sulfate, aluminum iron sulfate, aluminum ammonium sulfate, iron chloride, aluminum chloride, sodium chloride, zinc chloride, zinc phenol sulfate, tannic acids, adrenalin and mixtures thereof.

The invention moreover relates to a cap to form a chamber over a tooth and an adjacent outer part of the sulcus, for the retraction of sulcus from said tooth, preferably according to a process according to the invention as outlined above, characterized in that the borderline of the open end of the cap virtually resembles the natural wavelike boundary of sulcus surrounding a tooth, and that the cap is made from or essentially comprises a material selected from the group consisting of fibers, especially natural fibers, cotton, cellulose, open- and/or closed cell foam material, elastomeric silicone materials and mixtures thereof and mixtures thereof. Preferably, an outer section of said cap is reinforced, e.g. by a pressing process. Most preferably, the cap is made entirely from the same material.

Suchlike anatomically formed caps are not known in the prior art and proved especially useful for efficiently and reliably forming a chamber over a tooth, wherein said chamber comprises as its walls the tooth, the retraction cap and an outer section of said sulcus, said chamber allowing for a silicone material to expand into the crevice between sulcus and tooth. Especially caps made from or essentially comprising the above-mentioned materials on the one hand exhibit sufficient mechanical integrity to form said chamber, but on the other hand are deformable and/or flexible, especially under biting pressure, in order to assure a sufficiently smooth fit, preferably under pressure applied by a finger tip or biting pressure, that allows for directing at least part of the expanding silicone material into the gingival crevice.

According to a further embodiment of the cap according to the invention, the cap is made from or essentially comprises an elastomeric material, especially an elastomeric, cured silicone material, preferably crosslinkable by condensation, most preferably by addition reaction, characterized in that the Shore A hardness of the silicone material, as measured according to DIN 535052000-08, is in the range of about 30 to about 80, preferably about 40 to 70, most preferably about 50 to 60. A material, especially an elastomeric silicone material, with a Shore A hardness in the above-mentioned ranges fulfils both the requirement of being deformable and/or flexible, especially under biting pressure, in order to assure a sufficiently smooth fit, and the requirement of sufficient mechanical integrity and stability to allow for an efficient and reliable formation of a chamber over the tooth. On the other hand, there is no risk with a material of such hardness to affect gingival tissue under e.g. normal biting pressure applied to the cap by a patient.

According to yet a further embodiment of the cap according to the invention, the cap is made from or essentially comprises a foam material, characterized in that the compression hardness of the foam material, as measured according to DIN EN ISO 1798, is in the range of about 5 kPa to about 100 kPa, preferably about 30 kPa to about 70 kPa, most preferably 40 kPa to about 60 kPa, thereby providing a similarly balanced compromise of sufficient mechanical stability on the one hand, and deformability and/or flexibility on the other hand, as outlined above with respect to elastomeric silicone material.

The invention further relates to a dental kit for forming a chamber over a tooth and an adjacent outer part of the sulcus, especially suitable for widening of sulcus, comprising:

A cap, especially according to one of the claims, the borderline of the open end of said cap virtually resembling the natural wavelike boundary of sulcus surrounding a tooth; and at least one expandable, curable silicone material, wherein said silicone material exhibits a volume expansion of at least 20%, preferably at least 30% during or after curing as compared to the original volume of the non-cured silicone material.

The kit, preferably the silicone material, may comprise a hemostatic compound, most preferably a tannic acid. Other suitable hemostatic may be provided the kit and/or the silicone material, such as those listed above with respect to the description of the process according to the invention.

The curable and expandable silicone material is preferably selected from the group of silicones crosslinkable by addition reactions. Other suitable silicone materials and additives may alternatively or additionally be provided in the kit, such as those listed above with respect to the description of the process according to the invention.

The invention moreover concerns a method of preparing a cap according to the invention for the retraction of sulcus from a tooth, especially according to a method according to the invention, comprising the step of at least partially filling said cap (an impression tray or a dental dam may also be used, where the dental situation allows for it) with a plastically deformable, especially malleable and/or flowable material, such as e.g. those commonly referred to as Putty-material. The cap is filled with the plastically deformable material prior, preferably immediately prior, to the application of the cap to the tooth, so that the plastically deformable material is not yet cured, crosslinked and/or set before application of the cap. As the material is still deformable, especially malleable and/or flowable, when the cap is applied, a smooth and reliable fit to tooth and sulcus and a circumferential contact to previously to the boundary of sulcus and tooth applied expandable silicone material can easily and reliably established. Thus, the plastically deformable material is preferably applied in a sufficient amount to allow for an intimate contact of said plastically deformable material to the boundary of the tooth and adjacent sulcus, when said cap is applied onto a prepared tooth, especially an intimate contact to an expandable silicone material previously applied onto and/or at the vicinity of said boundary of a tooth and adjacent sulcus. The plastically deformable material may be any impression material routinely applied in dentistry, e.g. a Putty-material; however, condensation- or, preferably, addition-crosslinkable materials, are preferred, most preferably addition-crosslinkable silicone materials. Addition-crosslinkable silicone materials are especially preferred because they result in a sufficient stick to the expandable silicone material, thereby facilitating a release of both silicone materials especially in one-piece after curing. Of course, additionally or alternatively to said plastically deformable material, the silicone material that cures and expands, particularly expands during or after its curing reaction, may be at least partially filled into the cap. Thuslike, the appliance of the expandable silicone material to the sulcus is even more facilitated, especially in case of dental restorations of two or more teeth to be prepared.

A preferred embodiment of the invention will now be described in more detail and on the basis of schematical figures, without the invention being limited thereto.

FIG. 1. Close-up view of gingival surrounding a tooth, prepared for restoration;

FIG. 2:(a) expandable silicone material being applied onto the sulcus of a tooth;

(b) cap, partially filled with a plastically deformable material, being applied onto said tooth.

(c) expansion of silicone material into the crevice of the sulcus;

(d) exposed sulcus after displacement of cap and expanded silicone material.

FIG. 3:(a) expandable silicone material being applied onto the sulcus of a tooth;

(b) deformable cap, being applied onto said tooth.

(c) expansion of silicone material into the crevice of the sulcus;

(d) exposed sulcus after displacement of cap and expanded silicone material.

FIG. 4:(a) anatomically formed, deformable cap with wavelike boundary at open end;

(b) side view along length-axis in a cross-sectional view, partly layed-open;

(c) side view along length-axis in a cross-sectional view, rotated by 90° compared to (b), partly layed-open.

As shown in FIG. 1, a tooth 1 is surrounded by gingival tissue 2. At the upper boundary of gingiva 2 and tooth 1, the slight crevice between tooth 1 and gingiva 2 is commonly referred to as sulcus 3. Thus, for the purpose of the forthcoming explanations, there is an outer section 2a and an inner section 2b of said gingiva 2, as more expressly shown in FIG. 1 than normally naturally occurring.

According to a first embodiment of the present invention, an expandable silicone material 4 is applied onto and/or at the vicinity of the boundary of a preferably previously prepared tooth 1 for receiving a dental restoration and adjacent sulcus 3 and/or gingival 2, preferably by means of a conventional double-barrel mixing cartridge 5 (FIG. 2(a)). Afterwards, a cap 6A e.g. such as a dental dam or an impression tray or an only one-side open, cylindrical cap for only one tooth, is applied onto said tooth 1, thereby forming a chamber over said silicone material 4, wherein said chamber comprises as its walls the tooth 1, the cap 6 and an outer section 2a of said gingiva 2 (FIG. 2(b)). Said cap 6A is filled immediately prior to insertion onto the tooth with a plastically deformable, malleable material 7, such as e.g. Affinis® Putty Super Soft (Coltène Whaledent). When applied onto the tooth, the plastically deformable material is still flowable and not yet cured, crosslinked or set. As suitable plastically deformable material, common silicone-based dental impression materials can be employed. The formation of a chamber over the tooth, reaching out to an outer section 2a of the gingiva 2, allows for the silicone material 4 to expand into the sulcus 3 and to thereby retract the sulcus (3) from the tooth (FIG. 2(c)). After sufficient or complete expansion of the silicone material 4 into the sulcus 3, the cap 6A can be easily removed together with the previously applied plastically deformable material 7 and the expanded silicone material 4, thus leaving a wide opened sulcus, ready for further dental manipulations for dental restoration (FIG. 2(d)). Of course, the expandable silicone material 4 may also be applied onto the sulcus 3 by filling it into the cap 6A prior to putting the cap onto the tooth (not shown in detail). Also, mixtures of a plastically deformable material 7 and an expandable silicone material 4 may be provided in the cap, either in layers or mixed. In any case, although expandable silicone is provided by being filled into the cap prior to putting the cap onto the tooth, additional expandable silicone material may be advantageously applied onto the sulcus 3.

According to another embodiment of the present invention, which may be employed alternatively or in combination with the aforementioned embodiment, an especially under biting pressure deformable cap 6B is used. Thereby, the cap 6B may thus more easily be fitted onto the outer section 2a of the gingiva 2, albeit the natural wavelike contour of the sulcus. Again, the expandable silicone material 4 is applied onto or in the vicinity of the sulcus 3 (FIG. 3(a)). A deformable cap 6B is positioned onto the tooth 1, thereby forming a chamber comprising as its walls the tooth 1, the deformable cap 6B and an outer section 2a of the gingival 2 (FIG. 3(b)). Preferably, an outer layer of said cap 6B is reinforced, and an inner layer 9 is more loosely constituted in order to allow for an easy fitting onto the prepared tooth and simultaneously for an at least loose filling of remaining space between cap 6B and tooth 1, thus even more efficiently directing an expanding material 4 into the sulcus 3. Upon expansion of the silicon material 4, the crevice of the sulcus is widened (FIG. 3(c)). After removal of the cap 6B and the expandable silicone material 4, the sulcus 3 is widely retracted and the tooth 1 ready for further manipulations in dental restoration.

FIGS. 4(a), (b) and (c) illustrate a cap 6 according to the invention, which cap possesses a borderline 8 of the open end that virtually resembles the natural wavelike boundary of sulcus 3 surrounding a tooth 1. Thereby, a more reliable contact to the gingiva can be established, which is also of high importance for the method of sulcus retraction according to the invention. Preferably, the cap 6B is made from or essentially comprises a material selected from the group consisting of fibers, especially natural fibers, cotton, cellulose, open- and/or closed cell foam material, elastomeric silicone materials and mixtures thereof. Thuslike, a suitable compromise of mechanical stability and integrity on the one hand, and deformability and/or flexibility on the other hand can easily be achieved. Most preferably, only an outer layer of said cap 6B is reinforced, and an inner layer 9 is more loosely constituted in order to allow for an easy fitting onto the prepared tooth and simultaneously for an at least loose filling of remaining space between cap and tooth, thus even more efficiently directing an expanding material into the sulcus, when the cap is used in a method for sulcus retraction according to the invention.

What is claimed is:

1. A dental cap to form an enclosed chamber over a tooth having a wavelike boundary with the sulcus surrounding the tooth, the cap having a single open end, and having a borderline at said open end wherein said borderline virtually resembles the wavelike boundary of the sulcus surrounding the tooth being enclosed, the cap being formed entirely of the same fiber material and having an outer layer and an inner layer with the outer layer being reinforced and the inner layer remaining more loosely and constituted, such that the cap is deformable but provides sufficient mechanical rigidity to transmit a force into the sulcus surrounding the tooth.

2. A cap as in claim 1, wherein the outer layer o the fiber material is pressed to form the reinforced outer layer attached to the inner layer.

* * * * *